United States Patent
Masticola et al.

(10) Patent No.: US 7,447,333 B1
(45) Date of Patent: Nov. 4, 2008

(54) VIDEO AND AUDIO MONITORING FOR SYNDROMIC SURVEILLANCE FOR INFECTIOUS DISEASES

(75) Inventors: Stephen P. Masticola, Kingston, NJ (US); David Volk Beard, Inkom, ID (US); Dorin Comaniciu, Princeton Jct., NJ (US); Justinian Rosca, West Windsor, NJ (US)

(73) Assignee: Siemens Corporate Research, Inc., Princeton, NJ (US)

( * ) Notice: Subject to any disclaimer, the term of this patent is extended or adjusted under 35 U.S.C. 154(b) by 867 days.

(21) Appl. No.: 11/037,914

(22) Filed: Jan. 18, 2005

Related U.S. Application Data

(60) Provisional application No. 60/538,347, filed on Jan. 22, 2004.

(51) Int. Cl.
*G06K 9/00* (2006.01)
*G08B 23/00* (2006.01)

(52) U.S. Cl. .................... 382/103; 382/128; 340/573.1; 348/143

(58) Field of Classification Search ................. 382/103, 382/128; 348/143, 159; 705/2; 706/924; 340/500, 501, 573.1, 825.36, 825.49
See application file for complete search history.

(56) References Cited

U.S. PATENT DOCUMENTS

2004/0024612 A1 * 2/2004 Gerntholtz ..................... 705/2
2004/0141636 A1 * 7/2004 Liang et al. ................. 382/110
2004/0236604 A1 * 11/2004 McNair ........................ 705/2

OTHER PUBLICATIONS

Dorin Comaniciu, et al., Kernel-Based Object Tracking, IEEE Transactions on Pattern Analysis and Machine Intelligence, vol. 25, No. 5, pp. 564-575 2003.
Dorin Comaniciu, An Algorithm for Data-Driven Bandwidth Selection, IEEE Transactions Pattern Analysis and Machine Intelligence, vol. 25, No. 2, pp. 281-288, 2003.
Dorin Comaniciu, et al., Adaptive Resolution System for Distributed Surveillance, Real-Time Imaging, vol. 8, No. 5, pp. 427-437, 2002.
Michael Greiffenhage, et al., Design, Analysis and Engineering of Video Monitoring Systems: an Approach and a Case Study, Proceedings of the IEEE on Third Generation Surveillance Systems, vol. 89, No. 10, pp. 1498-1517, 2001.

(Continued)

*Primary Examiner*—Andrew W Johns
(74) *Attorney, Agent, or Firm*—Donald B. Paschburg; F. Chau & Associates, LLC

(57) ABSTRACT

We present, in exemplary embodiments of the present invention, novel systems and methods for syndromic surveillance that can automatically monitor symptoms that may be associated with the early presentation of a syndrome (e.g., fever, coughing, sneezing, runny nose, sniffling, rashes). Although not so limited, the novel surveillance systems described herein can be placed in common areas occupied by a crowd of people, in accordance with local and national laws applicable to such surveillance. Common areas may include public areas (e.g., an airport, train station, sports arena) and private areas (e.g., a doctor's waiting room). The monitored symptoms may be transmitted to a responder (e.g., a person, an information system) outside of the surveillance system, such that the responder can take appropriate action to identifying, treat and quarantine potentially infected individuals, as necessary.

20 Claims, 2 Drawing Sheets

OTHER PUBLICATIONS

Dorin Comaniciu, Nonparametric Information Fusion for Motion Estimation, IEEE International Conference Computer Vision and Pattern Recognition, Madison, Wisconsin, vol. 1, pp. 59-66, 2003.

Binglong Xie, et al., Component Fusion for Face Detection in the Presence of Heteroscedastic Noise, Annual Conference of the German Society for Pattern Recognition (DAGM'03), Magdeburg, Germany, 2003.

Dorin Comaniciu, Bayesian Kernel Tracking, Annual Conference of the German Society for Pattern Recognition (DAGM'02), Zurich, Switzerland, pp. 438-455, 2002.

Alessio Del Bue, et al., Smart Cameras With Real-Time Video Object Generation, IEEE International Conference Image Processing, Rochester, NY, vol. 3, pp. 429-432, 2002.

Dorin Comaniciu, et al., The Variable Bandwidth Mean Shift and Data-Driven Scale Selection, Nominated for Best Paper, IEEE International Conference Computer Vision, Vancouver, Canada, vol. 1, pp. 435-455, 2001.

Dorin Comaniciu, et al., Mean Shift and Optimal Prediction for Efficient Object Tracking, IEEE International Conference Image Processing, Vancouver, Canada, vol. 3, pp. 70-73, 2000.

Dorin Comaniciu, et al., Real-Time Tracking of Non-Rigid Objects Using Mean Shift, Best Paper Award, IEEE International Conference Computer Vision and Pattern Recognition, Hilton Head Island, South Carolina, vol. 2, 142-149, 2000.

Dorin Comaniciu, et al., Robust Detection and Tracking of Human Faces With an Active Camera, IEEE International Workshop on Visual Surveillance, Dublin, Ireland, 11-18, 2000.

Stefanie Aalburg, et al., Single-and Two-Channel Noise Reduction for Robust Speech Recognition in Car, In ISCA Tutorial and Research Workshop on Multi-Modal Dialogue in Mobile Environments, Stuttgart, Jun. 2002.

Radu Balan, et al., AR Processes and Sources can be Reconstructed From Degenerate Mixtures, In Proceedings ICA '99, Aussois, pp. 467-472, 1999, Aussois, France.

Radu Balan, et al., Statistical Properties of STFT Ratios for Two Channel Systems and Applications to Blind Source Separation, In Petteri Pajunen and Juha Karhunen, editors, Proceedings ICA 2000, Helsinki, pp. 429-434, Otamedia 2000, Helsinki, Finland, Jun. 2000.

Radu Balan, et al., Microphone Array Speech Enhancement by Bayesian Estimation of Spectral Amplitude and Phase, In Proceedings of SAM 2002, Rosslyn VA, 2002.

Radu Balan, et al., Robustness of Parametric Source Demixing in Echoic Environments, In 3$^{rd}$ International Conference on Independent Component Analysis and Blind Source Separation (ICA2001), San Diego, CA, Dec. 2001.

Radu Balan, et al., Non-Square Blind Source Separation Under Coherent Noise by Beamforming and Time-Frequency Masking, In Proceedings of the 4$^{th}$ International Conference on Independent Component Analysis and Blind Source Separation (ICA2003), Nara Japan, Apr. 2003.

Radu Balan, et al., Scalable Non-Square Blind Source Separation in the Presence of Noise, In IEEE International Conference on Acoustics, Speech, and Signal Proceeding (ICASSP2003), Hong-Kong, China, Apr. 2003.

Radu Balan, et al., The Influence of Windowing on Time Delay Estimates, In Proceedings CISS 2000, Princeton, NJ, 2000, Princeton.

Alexander Jourjine, et al., Blind Separation of Disjoint Orthogonal Signals: Demixing N Sources From 2 Mixtures, In Proceedings IEEE International Conference on Acoustics, Speech and Signal Processing. IEEE Press, 2000, Jun. 5-9, 2000, Istanbul, Turkey.

Scott Rickard, et al., Real-Time Time-Frequency Based Blind Source Separation, In 3$^{rd}$ International Conference on Independent Component Analysis and Blind Source Separation (ICA2001), San Diego, CA, pp. 651-656, Dec. 2001.

Scott Rickard, et al., Blind Source Separation Based on Space-Time-Frequency Diversity, in Proceedings of the 4$^{th}$ International Conference on Independent Component Analysis and Blind Source Separation (ICA2003), Nara, Japan, Apr. 2003.

Scott Rickard, et al., On the Approximate W-Disjoint Orthogonality of Speech, In IEEE International Conference on Acoustics, Speech and Signal Processing (ICASSP2002), Orlando, Florida, USA, vol. 1, pp. 529-532, May 2002.

Justinian Rosca, et al., Multi-Channel Psychoacoustically Motivated Speech Enhancement, In IEEE International Conference on Acoustics, Speech and Signal Processing, (ICASSP2003), Hong-Kong, China Apr. 2003.

Justinian Rosca, et al., Multichannel Voice Detection in Adverse Environments, In Proceedings of EUSIPCO 2002, 2002.

Justinian Rosca, et al., Real-Time Audio Source Separation by Delay and Attenuation Compensation in the Time Domain, In ICA 2001, 2001.

Justinian Rosca, et al., Cepstrum-Like ICA Representation for Text Independent Speaker Recognition, In Proceedings of the 4$^{th}$ International Conference on Independent Component Analysis and Blind Source Separation (ICA2003), Nara, Japan Apr. 2003.

Justinian Rosca, et al., Broadband Direction-of-Arrival Estimation Based on Second Order Statistics, In S.A. Solia, T.K. Leen and K-R Muller, editors, Advances in Neural Information Processing Systems 12, pp. 775-781, MIT Press, 2000.

* cited by examiner

VIDEO AND AUDIO MONITORING FOR SYNDROMIC SURVEILLANCE FOR INFECTIOUS DISEASES

CROSS-REFERENCE TO RELATED APPLICATIONS

This application claims priority to U.S. Provisional Application No. 60/538,347, which was filed on Jan. 22, 2004, and which is fully incorporated herein by reference.

BACKGROUND OF THE INVENTION

1. Field of the Invention

The present invention relates generally to the field of syndromic surveillance, and, more particularly, to automated behavioral video and audio monitoring for infectious diseases.

2. Description of the Related Art

Fear of infectious diseases and bioterrorism events is a cause for concern among many in today's social landscape. For example, during November 2002 through July 2003, a total of 8,098 people worldwide became sick with severe acute respiratory syndrome ("SARS") that was accompanied by either pneumonia or respiratory distress syndrome (probable cases), according to the World Health Organization ("WHO"). Of these, 774 died. For another example, between September and October 2001, letters containing *Bacillus anthracis* (known commonly as "anthrax") were received by mail in several parts of the United States. A widespread scare of handling United States mail soon ensued.

Fortunately, infectious outbreaks for both of the above examples were contained before the public health was substantially jeopardized. However, it is well-accepted that future outbreaks of infectious disease and bioterrorism events, which can rapidly spread without notice, may not be so easily contained without earlier detection and response. Controlling rapidly-spreading, infectious diseases and sicknesses require that infected individuals be promptly identified, treated and quarantined, if necessary, to prevent further outbreak.

Syndromic surveillance is a methodology for finding individuals who manifest a syndrome (i.e., a collection of symptoms) associated with a disease or sickness. For infectious diseases, syndromic surveillance can provide a source of infection and prevent further outbreak. For bioterrorism events, syndromic surveillance can provide early detection of widespread dissemination of bioterrorism agents, prompting life-saving treatment of those infected and timely containment of the deadly agents.

Traditional syndromic surveillance technology generally relies on manual reporting of symptoms, syndromes, and diagnoses by health care workers. One difficulty with this approach is that a patient may wait before diagnosis and treatment of the infectious disease or sickness. If the patient waits too long, the patient may not receive potentially life-saving treatment in time. If a patient has an infectious disease, the wait may allow the patient to infect several other people prior to seeking adequate health care. If a patient is sick because of a bioterrorism event, the wait may postpone the determination by health officials of the bioterrorism event. These difficulties, among others, substantially limit the effectiveness of traditional syndromic surveillance.

SUMMARY OF THE INVENTION

In one aspect of the present invention, a method for syndromic surveillance is provided. The method includes the steps of detecting syndromic data associated with infectious disease and sickness among a plurality of people using a plurality of monitoring devices; probabilistically fusing the syndromic data from the plurality of monitoring devices; locating individuals exhibiting the syndromic data; verifying the locations of the individuals and the syndromic data for consistency among the plurality of monitoring devices; and transmitting the location of a potentially infected individual exhibiting the probabilistically fused syndromic data to a responder for tracking the potentially infected individual.

In another aspect of the present invention, a system for syndromic surveillance is provided. The system includes a plurality of symptom monitors, wherein the plurality of symptom monitors detect a plurality of symptoms among a plurality of people, and wherein at least one of the plurality of symptom monitors detects a location for at least one candidate from the plurality of people exhibiting at least one of the plurality of symptoms; a syndrome identifier operatively connected to the plurality of symptom monitors, wherein the syndrome identifier identifies a combination of symptoms exhibited by a potentially infected individual in the at least one candidate, wherein the combination of symptoms indicates a syndrome, and wherein the syndrome identifier at least one of verifies and assists the plurality of symptom monitors; a position tracker operatively connected to the syndrome identifier for continuously tracking the potentially infected individual; and a response system for transmitting the tracking information of the potentially infected individual and the results of the syndrome identifier to a responder.

In yet another aspect of the present invention, a machine-readable medium having instructions stored thereon for execution by a processor to perform a method for syndromic surveillance is provided. The method includes the steps of detecting syndromic data associated with infectious disease and sickness among a plurality of people using a plurality of monitoring devices; probabilistically fusing the syndromic data from the plurality of monitoring devices; locating individuals exhibiting the syndromic data; verifying the locations of the individuals and the syndromic data for consistency among the plurality of monitoring devices; and transmitting the location of a potentially infected individual exhibiting the probabilistically fused syndromic data to a responder for tracking the potentially infected individual.

BRIEF DESCRIPTION OF THE DRAWINGS

The invention may be understood by reference to the following description taken in conjunction with the accompanying drawings, in which like reference numerals identify like elements, and in which.

DETAILED DESCRIPTION OF PREFERRED EMBODIMENTS

Figure 1:
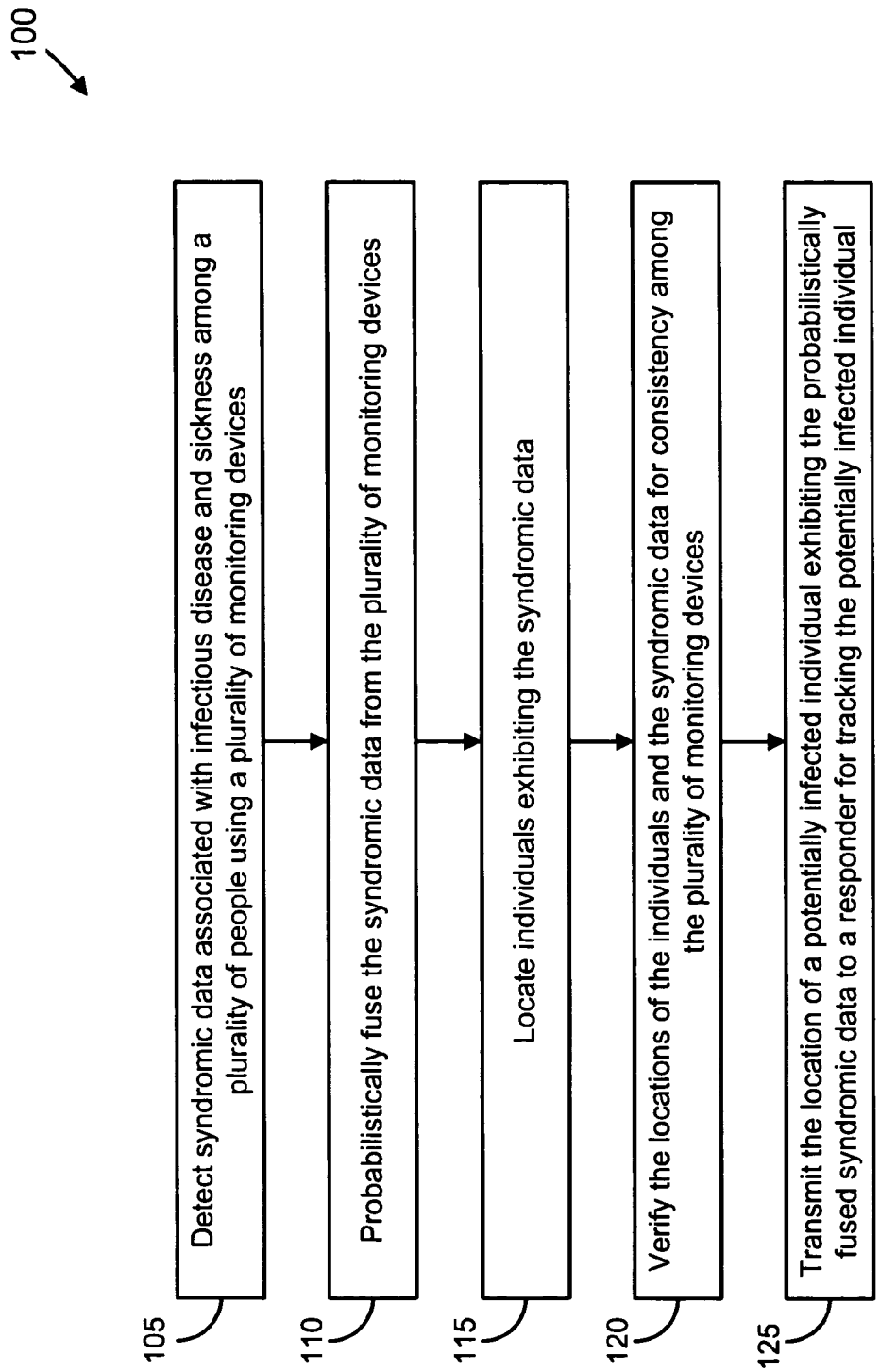
FIG. 1 depicts a method for syndromic surveillance, in accordance with one exemplary embodiment of the present invention.

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

It is to be understood that the systems and methods described herein may be implemented in various forms of hardware, software, firmware, special purpose processors, or a combination thereof. In particular, at least a portion of the present invention is preferably implemented as an application comprising program instructions that are tangibly embodied on one or more program storage devices (e.g., hard disk, magnetic floppy disk, RAM, ROM, CD ROM, etc.) and executable by any device or machine comprising suitable architecture, such as a general purpose digital computer having a processor, memory, and input/output interfaces. It is to be further understood that, because some of the constituent system components and process steps depicted in the accompanying Figures are preferably implemented in software, the connections between system modules (or the logic flow of method steps) may differ depending upon the manner in which the present invention is programmed. Given the teachings herein, one of ordinary skill in the related art will be able to contemplate these and similar implementations of the present invention.

We present, in exemplary embodiments of the present invention, novel systems and methods for syndromic surveillance that can automatically monitor symptoms that may be associated with the early presentation of a syndrome (e.g., fever, coughing, sneezing, runny nose, sniffling, rashes). Although not so limited, the novel surveillance systems described herein can be placed in common areas occupied by a crowd of people, in accordance with local and national laws applicable to such surveillance. Common areas may include public areas (e.g., an airport, train station, sports arena) and private areas (e.g., a doctor's waiting room). The monitored symptoms may be transmitted to a responder (e.g., a person, an information system) outside of the surveillance system, such that the responder can take appropriate action for identifying, treat and quarantine potentially infected individuals, as necessary.

Referring now to FIG. 1, a method 100 for syndromic surveillance is shown, in accordance with one exemplary embodiment of the present invention. Syndromic data associated with infectious disease and sickness is detected (at 105) among a plurality of people using a plurality of monitoring devices. The detected data may include physical data associated with the infectious disease or sickness. For example, temperature-related symptoms (e.g., fever, hypothermia) may be detected using an infrared video device, audible symptoms (e.g., coughing, sneezing, sniffling) may be detected using an audio monitoring device, and visual symptoms (e.g., head movement associated with coughing and sneezing, runny nose, rashes, watery eyes) may be detected using a video monitoring device. It should appreciated that many symptoms, such as coughing and sneezing, exhibit themselves in a variety of manners (e.g., audio, visual).

Although not so limited, coughing and fever are used throughout the present disclosure for the sake of simplicity. It should be appreciated that any of a variety of symptoms associated with any of a variety of infectious diseases and sicknesses may be monitored using any of a variety of monitoring devices, as contemplated by those skilled in the art.

The syndromic data from the plurality of monitoring devices is probabilistically fused (at 110). For example, a subset of the syndromic data detected from a single individual may indicate a syndrome with the individual. Not all individuals will indicate all possible symptoms of a syndrome. Further, certain symptom indications may not be as severe as others. Thus, the accuracy of the syndrome determination may be indicated using a probabilistic scale. Information necessary to determine the probabilistic scale may be obtained from any of a variety of resources, such as medical literature.

The individuals exhibiting the syndromic data are located (at 115). In one embodiment, as described in greater detail below, the individuals may be located, for example, using data collected from a plurality of monitoring devices, such as a audio monitoring device and a video monitoring device.

The locations of the individuals and the syndromic data are verified (at 120) for consistency among the plurality of monitoring devices. For example, an audio monitoring device and a video monitoring device may each independently determine the location of a coughing source. The audio monitoring device may determine location, for example, by positioning a sufficient number of receivers in a room to determine the angle and direction of the cough. The video monitoring device may determine location, for example, by dividing the monitored area into a coordinate system. In one embodiment, the coordinate-based system and the positioning of the receivers may be synchronized accordingly. By comparing the results from the audio monitoring device with the video monitoring device, the accuracy and reliability of the detected data can be verified. For example, if the determined angle and direction of a cough from the audio monitoring device is consistent with the location from the video monitoring device of a jerking head associated with the cough, then the coughing data may be determined to be accurate and reliable. It should be appreciated that an increased number of monitoring devices in a particular area may provide more accurate and reliable results.

The location of a potentially infected individual exhibiting the probabilistically fused syndromic data is transmitted (at 125) to a responder for tracking the potentially infected individual. In one embodiment the responder may be a health official receiving the location of the potentially infected individual and the syndromic data through a portable response system that continuously tracks the potentially infected individuals. In an alternate embodiment, the responder may be an automated response system. By tracking the infected individuals, the responder can easily identify, treat and quarantine, if necessary, the potentially infected individuals.

Figure 2:
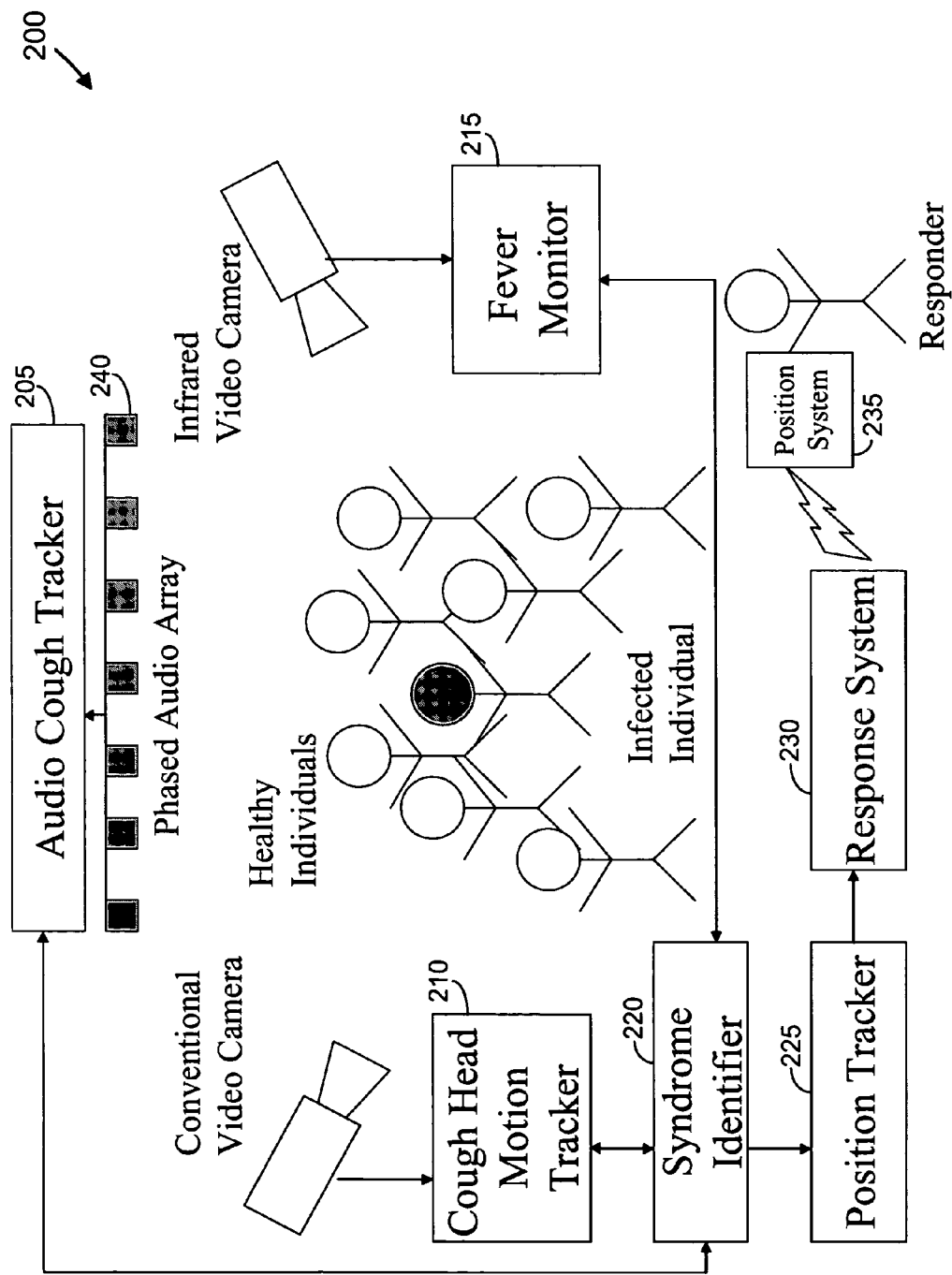
FIG. 2 depicts a system for syndromic surveillance, in accordance with one exemplary embodiment of the present invention.

Referring now to FIG. 2, a syndromic surveillance system 200 is shown, in accordance with one embodiment of the present invention. The syndromic surveillance system 200 includes an audio cough tracker 205, a cough head motion tracker 210, and a fever monitor 215. A syndrome identifier 220 is operatively connected to the audio cough tracker 205, the cough head motion tracker 210, and the fever monitor 215. The syndrome identifier 220, as shown in FIG. 2, can receive data from and transmit data to the audio cough tracker 205, the cough head motion tracker 210, and the fever monitor 215. The syndrome identifier 220 is operatively connected to a position tracker 225. The position tracker 225 is operatively connected to a response system 230. The response system 230 is operatively connected to a position system 235 and responder. Although not so limited, as shown in FIG. 1, the position system 235 wirelessly transmits data to the responder.

As shown in FIG. 2, the audio cough tracker 205 is operatively connected to phased audio array 240. The phased audio array 240 includes a plurality of receivers for receiving sound candidates. The phased audio array 240 may be present, for example, in a room in a three-dimensional configuration. It should be appreciated that the phased audio array 240 may be configured in any of a variety of configurations, as contemplated by those skilled in the art. Ideally, the phased audio array 240 should be configured in such a manner that necessary information can be properly derived from the sound candidates. For example, in one embodiment, the phased audio array 240 may be configured such that the angle and direction of the sound candidates can be accurately determined.

When the audio cough tracker 205 receives a sound candidate, the sound candidate may be a sound mixture that includes background noise, such as crowd noise, in addition to a plurality of audible symptoms. In such a case, the audible symptoms (in this case, coughing sounds) may be separated from each other and from the background noise using any of a variety of demixing and noise reduction techniques known to those skilled in the art, such as blind source separation. The accuracy of blind source separation techniques may depend on a good directionality of the sound candidate in combination with the number of sound sources active at a given time. Thus, a good configuration of the phased audio array 240 may be imperative for accurate blind source separation.

The audio cough tracker 205 may differentiate between different types of coughs as well as between a cough sound and a non-cough sound by comparing a detected audible symptom with known data, such as a database of audible cough samples. Alternate embodiments of the present invention may include neural networks, as well as other artificial intelligence mechanisms and techniques, for "learning" audible symptoms in a variety of applications.

The audio cough tracker 205 may determine the location of the source/sources of the audible symptoms using any of a variety of source localization techniques known to one skilled in the art. For example, the phased audio array 240 may be configured in such a manner that the location of the source can be determined by analyzing the direction and angle of the sound candidate. The audio cough tracker 205 may also record the time when each cough occurs.

The cough head motion tracker 210 identifies individuals who show jerking head motions related to coughing. As shown in FIG. 2, the cough head motion tracker 210 is operatively connected to a motion video camera. In one embodiment, the cough head motion tracker 210 may analyze the recorded video for head motions related to coughing. Heads of individuals in the video may be isolated using any of a variety of video recognition techniques known to those skilled in the art.

The cough head motion tracker 210 may differentiate between different types of coughing head motions as well as between cough head motions and non-cough head motions by comparing the recorded video with known data, such as a database of cough head motions. Alternate embodiments of the present invention may include neural networks, as well as other artificial intelligence mechanisms and techniques, for "learning" cough head motions in a variety of applications.

The cough head motion tracker 210 may be an application of an object tracking system, such as the one provided in U.S. patent application Ser. No. 10/325,413, entitled "REAL-TIME VIDEO OBJECT GENERATION FOR SMART CAMERAS," filed on Dec. 20, 2002, which is incorporated herein by reference.

The cough head motion tracker 210 may determine the location of the source/sources of the cough by using any of a variety of techniques known to one skilled in the art. For example, the entire physical area recorded by the cough head motion tracker 210 may be divided into a three-dimensional grid. Thus, the location of the source may be recorded using a coordinate system based on the three-dimensional grid. The cough head motion tracker 210 may also record the time when each cough occurs.

The fever monitor 215 identifies individuals who may be showing signs of a fever. As shown in FIG. 2, the fever monitor 215 is operatively connected to an infrared video camera, which can determine an individual's temperature. The fever monitor 215 may also locate individuals. For example, the entire physical area recorded by the fever monitor 215 may be divided into a three-dimensional grid. Thus, the location of the source may be recorded using a coordinate system based on the three-dimensional grid. The fever monitor 215 may also record the time when each temperature reading is recorded.

Data from the audio cough tracker 205, the cough head motion tracker 210, and the fever monitor 215 is transmitted to the syndrome identifier 220. In one embodiment, the audio cough tracker 205, the cough head motion tracker 210 and the fever monitor 215 may each utilize the data of the other monitoring devices for verification and assistance via the syndrome identifier 220. For example, the location of a cougher determined by the cough head motion tracker 210 may be compared to the location of the cougher determined by the audio cough tracker 205. Further, data from the verification may be used to enhance the sensitivity and selectivity of the monitoring devices. In one embodiment, the location system used by the audio cough tracker 205 and the cough head motion tracker 210 may be synchronized. For another example, the location of a cougher determined by the cough head motion tracker 210 may be used to assist the audio cough tracker 205 in determining the location of the cougher.

The syndrome identifier 220 may analyze the collected data from the various monitoring devices (e.g., the audio cough tracker 205, the cough head motion tracker 210, and the fever monitor 215) to determine whether detected individuals have combined symptoms (i.e., a syndrome), which potentially indicates a more serious illness. Whether the same individual is detected by more than one monitoring device may be determined using any of a variety of factors, such as the location of the detected individual and the time recorded when the symptom was exhibited.

The position tracker 225 receives the analyzed data from the syndrome identifier 220. The position tracker 225 continuously tracks the individuals identified to have the syndrome(s) detected by the syndrome identifier. The position tracker 225 may track the individuals using, for example, the location determining capabilities of the various monitoring devices operatively connected to the syndrome identifier 220. As described in greater detail above, the various monitoring devices may utilize the capabilities of each other to verify and assist tracking the location of the identified individuals.

The output of the position tracker is transmitted to the response system 230, which, as shown in FIG. 2, transmits the locations of the identified individuals to a portable position systems 235 held by the responder. Although not so limited, the locations of the identified individuals are transmitted wirelessly. In alternate embodiments, the locations of the identified individuals are transmitted by other means, such as telephone lines and Ethernet. The responder may also receive the results of the syndrome identifier such that the responder knows what type of syndrome(s) the identified individuals may possess. The responder can track and rendezvous with possibly-infected individuals.

It should be appreciated that the components shown in FIG. 2 are only exemplary. For example, components may be combined or divided depending on a particular implementation. Further, the number and types of monitoring and tracking devices may differ depending on a particular implementation.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method for syndromic surveillance, comprising:
   detecting syndromic data associated with infectious disease and sickness among a plurality of people using a plurality of monitoring devices;
   probabilistically fusing the syndromic data from the plurality of monitoring devices;
   locating individuals exhibiting the syndromic data;
   verifying the locations of the individuals and the syndromic data for consistency among the plurality of monitoring devices; and
   transmitting the location of a potentially infected individual exhibiting the probabilistically fused syndromic data to a responder for tracking the potentially infected individual.

2. The method of claim 1, wherein the step of probabilistically fusing the syndromic data comprises detecting a combination of symptoms exhibited by a single individual, the combination of symptoms being associated with a syndrome.

3. The method of claim 1, wherein the step of detecting syndromic data comprises detecting at least one of temperature-related symptoms, audible symptoms, and visual symptoms.

4. The method of claim 1, further comprising:
   enhancing sensitivity and selectivity of the plurality of monitoring devices using the results of the step of verifying.

5. The method of claim 1, wherein the step of transmitting the location of a potentially infected individual to a responder comprises wirelessly transmitting the location of the potentially infected individual to the responder.

6. The method of claim 1, wherein the step of transmitting the location of a potentially infected individual to a responder comprises transmitting the location of the potentially infected individual to a portable receiver operated by the responder.

7. The method of claim 1, further comprising:
   transmitting the probabilistically fused syndromic data to the responder.

8. The method of claim 1, further comprising:
   transmitting the syndromic data to the responder.

9. A system for syndromic surveillance, comprising:
   a plurality of symptom monitors, wherein the plurality of symptom monitors detect a plurality of symptoms among a plurality of people, and wherein at least one of the plurality of symptom monitors detects a location for at least one candidate from the plurality of people exhibiting at least one of the plurality of symptoms;
   a syndrome identifier operatively connected to the plurality of symptom monitors, wherein the syndrome identifier identifies a combination of symptoms exhibited by a potentially infected individual in the at least one candidate, wherein the combination of symptoms indicates a syndrome, and wherein the syndrome identifier verifies the plurality of symptom monitors;
   a position tracker operatively connected to the syndrome identifier for continuously tracking the potentially infected individual; and
   a response system for transmitting the tracking information of the potentially infected individual and the results of the syndrome identifier to a responder.

10. The system of claim 9, wherein the plurality of symptom monitors comprise at least one of a temperature monitor, a motion monitor, and an audio monitor.

11. The system of claim 10, wherein the temperature monitor comprises an infrared video camera.

12. The system of claim 10, wherein the motion monitor comprises a conventional video camera.

13. The system of claim 10, wherein the audio monitor comprises a phased audio array.

14. The system of claim 9, wherein the results of verifying the plurality of symptom monitors is transmitted to the plurality of symptom monitors for enhancing sensitivity and selectivity of the plurality of symptom monitors.

15. The system of claim 9, wherein the syndrome identifier continuously transmits the location of the potentially infected individual to the position tracker.

16. The system of claim 9, wherein one of the plurality of symptom monitors receives assistance from the other of the plurality of symptom monitors for detecting the plurality of symptoms.

17. The system of claim 9, wherein the system monitor verifies the plurality of symptom monitors comprises the system monitor verifies one of the plurality of symptom monitors based on the others of the plurality of symptom monitors.

18. The system of claim 9, wherein the response system wirelessly transmits the tracking information of the potentially infected individual and the results of the syndrome identifier to the responder.

19. The system of claim 9, wherein the response system transmits the tracking information of the potentially infected individual and the results of the syndrome identifier to a portable receiving unit operated by the responder.

20. A machine-readable medium having instructions stored thereon for execution by a processor to perform a method for syndromic surveillance, the method comprising:
   detecting syndromic data associated with infectious disease and sickness among a plurality of people using a plurality of monitoring devices;
   probabilistically fusing the syndromic data from the plurality of monitoring devices;
   locating individuals exhibiting the syndromic data;
   verifying the locations of the individuals and the syndromic data for consistency among the plurality of monitoring devices; and
   transmitting the location of a potentially infected individual exhibiting the probabilistically fused syndromic data to a responder for tracking the potentially infected individual.

* * * * *